United States Patent
Rollat et al.

(10) Patent No.: US 6,689,346 B1
(45) Date of Patent: *Feb. 10, 2004

(54) RESHAPABLE HAIR STYLING COMPOSITION COMPRISING ACRYLIC COPOLYMERS

(75) Inventors: Isabelle Rollat, Paris (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/695,392

(22) Filed: Oct. 25, 2000

(51) Int. Cl.$^7$ .................................................. A61K 7/06
(52) U.S. Cl. ...................... 424/70.1; 424/400; 424/401; 424/70.11; 424/70.15; 424/70.16
(58) Field of Search ................................ 424/400, 401, 424/70.1, 70.11, 70.15, 70.16

(56) References Cited

U.S. PATENT DOCUMENTS

| | | |
|---|---|---|
| 3,577,517 A | 5/1971 | Kubot et al. |
| 3,660,561 A | 5/1972 | Shepherd et al. |
| RE29,871 E | 12/1978 | Papantoniou et al. |
| 4,172,122 A | 10/1979 | Kubik et al. |
| 4,196,190 A | 4/1980 | Gehman et al. |
| 4,300,580 A | 11/1981 | O'Neill et al. |
| 4,358,567 A * | 11/1982 | Hayama et al. ............. 525/293 |
| 4,552,755 A | 11/1985 | Randen |
| 4,762,703 A | 8/1988 | Abrutyn |
| 4,859,455 A | 8/1989 | Nowak, Jr. et al. |
| 4,963,348 A | 10/1990 | Bolich et al. |
| 4,978,527 A | 12/1990 | Brink et al. |
| 4,985,239 A | 1/1991 | Yahagi et al. |
| 5,019,377 A | 5/1991 | Torgerson |
| 5,026,540 A | 6/1991 | Dixon et al. |
| 5,104,642 A | 4/1992 | Wells et al. |
| 5,120,531 A | 6/1992 | Wells et al. |
| 5,120,532 A | 6/1992 | Wells et al. |
| 5,171,807 A | 12/1992 | Kopolow |
| 5,173,291 A | 12/1992 | Brink et al. |
| 5,219,559 A | 6/1993 | Kopolow |
| 5,238,736 A | 8/1993 | Tseng et al. |
| 5,413,775 A | 5/1995 | Hatfield et al. |
| 5,441,728 A | 8/1995 | Tsauer et al. |
| 5,460,804 A | 10/1995 | Krzysik |
| 5,501,851 A | 3/1996 | Mudge et al. |
| 5,516,508 A | 5/1996 | Thaman et al. |
| 5,518,712 A | 5/1996 | Stewart |
| 5,547,659 A | 8/1996 | Rinaldi et al. |
| 5,589,157 A | 12/1996 | Hatfield |
| 5,620,683 A | 4/1997 | Tong et al. |
| 5,658,558 A | 8/1997 | Schwartz |
| 5,662,892 A | 9/1997 | Bolich, Jr. et al. |
| 5,688,493 A | 11/1997 | Sugawara et al. |
| 5,730,966 A | 3/1998 | Torgerson et al. |
| 5,938,058 A | 8/1999 | Kim |
| 5,968,495 A | 10/1999 | Bolich, Jr. et al. |
| 5,997,886 A | 12/1999 | Peffly et al. |
| 6,149,898 A | 11/2000 | Peffly et al. |
| 6,168,866 B1 * | 1/2001 | Clark ........................... 428/421 |
| 6,214,328 B1 | 4/2001 | Chang et al. |
| 6,294,158 B1 | 9/2001 | Dupuis |
| 2002/0004035 A1 | 1/2002 | Bhatt et al. |
| 2002/0058754 A1 | 5/2002 | Engel et al. |

FOREIGN PATENT DOCUMENTS

| | | |
|---|---|---|
| EP | 0 201 342 | 12/1986 |
| EP | 0 299 025 | 1/1989 |
| EP | 0 524 346 | 1/1993 |
| EP | 0 694 565 | 1/1996 |
| EP | 0 761 199 | 3/1997 |
| EP | 0 985 401 | 3/2000 |
| EP | 0 985 405 | 3/2000 |
| EP | 1 174 113 | 1/2002 |
| FR | 2760360 | 9/1998 |
| JP | 48-48648 | 7/1973 |
| JP | 56-90006 | 7/1981 |
| JP | 57-50912 | 3/1982 |
| JP | 10-95714 | 4/1998 |
| JP | 10-203937 | 8/1998 |
| WO | WO 93/06816 | 4/1993 |
| WO | WO 94/02112 | 2/1994 |
| WO | WO 98/24825 | 6/1998 |
| WO | WO 98/25710 | 6/1998 |
| WO | WO 98/38969 | 9/1998 |
| WO | WO 98/51266 | 11/1998 |
| WO | WO 99/08652 | 2/1999 |
| WO | WO 99/63954 | 12/1999 |
| WO | WO 00/57846 | 10/2000 |
| WO | WO 02/09656 | 2/2002 |

OTHER PUBLICATIONS

Co–pending U.S. application No. 09/627,055; Title: Reshapable Hair Styling Composition Comprising Acrylic Emulsions, Inventors: Isabelle Rollat et al., U.S. Filing Date: Jul. 27, 2000.

Co–pending U.S. application No. 09/627,121; Title: Reshapable Hair Styling Composition Comprising Aqueous Colloidal Dispersions of Sulfonated Polyurethane Urea, Inventors: Isabelle Rollat et al., U.S. Filing Date: Jul. 27, 2000.

Derwent Abstract of JP 57–50912.

(List continued on next page.)

Primary Examiner—Thurman K. Page
Assistant Examiner—Charesse Evans
(74) Attorney, Agent, or Firm—Finnegan, Henderson, Farabow, Garrett & Dunner, L.L.P.

(57) ABSTRACT

A reshapable hair styling composition comprising at least one acrylic copolymer comprising: (a) units derived from at least one monomer chosen from (meth)acrylate esters of $C_4$ to $C_{18}$ straight and branched chain alkyl alcohols, (b) units derived from at least one monomer chosen from (meth) acrylate esters of saturated and unsaturated cyclic alcohols containing 6 to 20 carbon atoms, (c) optionally units derived from at least one monomer chosen from hydrophilic monomers, and (d) optionally units derived from at least one monomer other than (a), (b), and (c) monomers, wherein said composition provides a reshapable effect.

11 Claims, No Drawings

OTHER PUBLICATIONS

English language translation of JP 10–203937.
Dialog Abstract of JP 10–203937.
Derwent Abstract of JP 10–95714.
Derwent Abstract of JP 10–203937.
Derwent Abstract of JP 48–48648.
Derwent Abstract of JP 56–90006.
Co–pending U.S. application No. 10/023,330; Title: Reshapable Hair Styling Rinse Composition Comprising (METH-)Acrylic Copolymers, Inventors: Isabelle Rollat et al., U.S. Filing Date: Dec. 20, 2001.

Co–pending U.S. application No. 10/022,253; Title: Reshapable Hair Styling Non–Rinse Composition Comprising (METH)Acrylic Copolymers, Inventors: Isabelle Rollat et al., U.S. Filing Date: Dec. 20, 2001.

Derwent Abstract of EP 0 761 199.

Derwent Abstract of EP 1 174 113.

EPO Apr. 3, 2003 Search Report for EP 02 29 3142.

* cited by examiner

RESHAPABLE HAIR STYLING COMPOSITION COMPRISING ACRYLIC COPOLYMERS

The present invention relates to a reshapable hair styling composition.

Fixing the hairstyle is an important element in hair styling, and involves maintaining a shaping that has already been carried out, or simultaneously shaping and fixing the hair.

In accordance with the invention, the term "hair styling composition" relates to any kind of hair composition that can be used to effect hair styling, for example fixing compositions, shampoos, conditioners, permanent waving compositions, hair care products, and hair treatment products.

The most prevalent hair styling compositions on the cosmetic market for shaping and/or maintaining the hairstyle are spray compositions comprising a solution, usually alcohol- or water-based, and one or more materials, generally polymer resins. One of the functions of polymer resins is to form links between the hairs, these materials also being called fixatives, in a mixture with various cosmetic adjuvants. This solution is generally packaged either in an appropriate aerosol container, which is pressurized with the aid of a propellant, or in a pump flask.

Other known hair styling compositions include styling gels and mousses, which are generally applied to the wetted hair before brushing or setting it. In contrast to the conventional aerosol lacquers, these compositions have the disadvantage that they do not allow the hair to be fixed in a shape created before their application. In fact, these compositions are essentially aqueous and their application wets the hair and is therefore unable to maintain the initial shape of the hairstyle. In order to shape and fix the hairstyle, therefore, it is necessary to carry out subsequent brushing and/or drying.

Such hair styling compositions all have the same disadvantage that they do not allow the hairstyle to be later modified to a desired shape, which is other than that formed initially, without starting the styling and fixing operations again. Moreover, under various kinds of stress, the hairstyle has a tendency to take on an undesirable permanent set, which cannot easily be modified. Also in the styling process, one desires hair conditioning benefits, such as ease of combing and soft hair feel appearance.

A subject of the invention is a reshapable hair styling composition comprising at least one acrylic copolymer comprising: (a) units derived from at least one monomer chosen from (meth)acrylate esters of $C_4$ to $C_{18}$ straight and branched chain alkyl alcohols, (b) units derived from at least one monomer chosen from (meth)acrylate esters of saturated and unsaturated cyclic alcohols containing 6 to 20 carbon atoms, (c) optionally units derived from at least one monomer chosen from hydrophilic monomers, and (d) optionally units derived from at least one monomer other than (a), (b), and (c) monomers, wherein said composition provides a reshapable effect.

Another subject of the invention is a reshapable hair styling composition comprising at least one acrylic copolymer comprising: (a) from about 10 to about 85 weight percent of units derived from at least one monomer chosen from (meth)acrylate esters of $C_4$ to $C_{18}$ straight and branched chain alkyl alcohols, (b) from about 5 to about 70 weight percent of units derived from at least one monomer chosen from (meth)acrylate esters of saturated and unsaturated cyclic alcohols containing 6 to 20 carbon atoms, (c) from 0 to about 20 weight percent of units derived from at least one monomer chosen from hydrophilic monomers, and (d) optionally units derived from at least one monomer other than (a), (b), and (c) monomers, wherein said composition provides a reshapable effect.

The weight percentages of the (a), (b), and, if used, (c) monomers, are based on the total weight of the monomers used.

Another subject of the invention is a reshapable hair styling composition comprising at least one acrylic copolymer, as described above, wherein said reshapable hair styling composition is in the form of a spray, aerosol, mousse, gel, or lotion.

Another subject of the invention is an aerosol device comprising a vessel, which comprises: (1) an aerosol composition, which provides a reshapable effect and comprises a liquid phase comprising at least one composition comprising at least one acrylic copolymer, as described above, and a propellant, and (2) a dispenser.

Another subject of the invention is a method of cosmetically treating hair, comprising applying to the hair before, during, or after shaping of a hairstyle of said hair a composition comprising at least one acrylic copolymer, as described above, wherein said composition provides a reshapable effect.

Another subject of the invention is a method of reshaping hair, comprising: (1) applying to the hair before, during, or after the initial shaping of the hairstyle of a composition comprising at least one acrylic copolymer, as described above, wherein said composition provides a reshapable effect, and (2) thereafter shaping the hairstyle at least once, wherein no additional composition or heat is added.

Another subject of the invention is a reshapable hair styling composition comprising at least one acrylic copolymer comprising: (a) from about 20 to about 80 weight percent of units derived from ethyl hexyl (meth)acrylate, (b) from about 5 to about 65 weight percent of units derived from isobornyl acrylate, and (c) from about 1 to about 15 weight percent of units derived from (meth)acrylic acid, wherein the ratio of ethyl hexyl (meth)acrylate derived units to isobornyl acrylate derived units ranges from about 0.5:1 to about 6:1, wherein said composition provides a reshapable effect.

In one embodiment of the invention, such reshapable hair styling compositions may be in the form of an aqueous emulsion or dispersion. All emulsions comprise a continuous phase and at least one dispersed phase. The term "dispersion" means generally a multi-phase system where at least one phase contains discrete particles distributed throughout a bulk substance. In this invention, at least a portion of the polymer may exist as the discrete particle in an aqueous phase. Dispersions are possible through the use of certain components that are insoluble in the water system. By "dispersion," it is also meant that not necessarily the entire polymer needs to be water insoluble; some of the polymer can be soluble in the water mixture. It is preferable that the dispersion remains stable under ambient conditions.

The term "(meth)acrylate" is used to mean both acrylate and methacrylate.

The term "reshapable" hair styling composition means a hair styling composition providing hair styling that can be restored or modified without new material or heat being applied. For example, in order to restore or modify the hairstyle in case of "drooping" or loss of setting (dishevelment), no new materials, such as water or any form of fixing agent, or heat are required. Thus, to provide a "reshapable" effect means to provide a hair styling that can be restored or modified without new material or heat being applied. The efficacy of the composition can be long lasting, such as 10–24 hours, giving rise to a durable styling effect. Other terms, which may be synonymous with reshapable, include repositionable, remoldable, restyleable, rearrangable, and remodelable.

The (a) monomers constitute from about 10 to about 85 weight percent of the total amount of monomers used. In one embodiment, they may constitute from about 20 to about 80 weight percent of the total amount of monomers used. The (a) monomers may be chosen from (meth)acrylate esters of $C_4$ to $C_{18}$ straight and branched chain alkyl alcohols. In one embodiment, the (a) monomers may be is chosen from isooctyl (meth)acrylate, n-butyl (meth)acrylate, isobutyl (meth)acrylate, t-butyl (meth)acrylate, 2-methylbutyl (meth) acrylate, 2-ethylhexyl (meth)acrylate, n-octyl (meth) acrylate, isononyl (meth)acrylate, lauryl (meth)acrylate, octadecyl (meth)acrylate, and mixtures thereof. In another embodiment, the (a) monomers may be chosen from 2-ethylhexyl acrylate, n-butyl acrylate, isooctyl acrylate, 2-methylbutyl acrylate, and mixtures thereof.

The (b) monomers generally have a higher $T_g$ than the (a) monomers. They may constitute from about 5 to about 70 weight percent of the total amount of monomers used. In one embodiment, they may constitute from about 10 to about 70 weight percent of the total amount of monomers used. In another embodiment, they may constitute from about 5 to about 65 weight percent of the total amount of monomers used. The (b) monomers may be chosen from (meth)acrylate esters of saturated and unsaturated cyclic alcohols containing 6 to 20 carbon atoms. In one embodiment, the (b) monomers may be chosen from monofunctional (meth) acrylate esters of bridged cycloalkyl alcohols, having 6 to 20 carbon atoms, and aromatic alcohols. The cycloalkyl and aromatic groups may be substituted by groups chosen from $C_1$ to $C_6$ alkyl, halogen, cyano groups, and the like. In another embodiment, the (b) monomers are chosen from bicyclo[2.2.1]heptyl (meth)acrylate; adamantyl (meth) acrylate; 3,5-dimethyladamantyl (meth)acrylate; isobornyl (meth)acrylate; tolyl (meth)acrylate; phenyl (meth)acrylate; t-butylphenyl (meth)acrylate; 2-napthyl (meth)acrylate; benzyl methacrylate; cyclohexyl methacrylate; menthyl methacrylate; 3,3,5-trimethylcyclohexyl methacrylate; dicyclopentenyl (meth)acrylate; 2-(dicyclopentenyloxy)ethyl (meth)acrylate; and mixtures thereof.

The (c) monomers may be hydrophilic monomers. They may constitute from 0 to about 20 weight percent of the total amount of monomers used. In one embodiment, they may constitute from about 1 to about 15 weight percent of the total amount of monomers used. In another embodiment, they may constitute from 1 to about 10 weight percent of the total amount of monomers used. In one embodiment, the (c) monomers may be chosen from those monomers having hydroxyl, ether, amide, amine, carboxylic acid, sulfonic acid, and phosphonic acid functionalities. In another embodiment, the (c) monomers may be chosen from (meth) acrylamide, 2-ethoxyethyl (meth)acrylate, mono (meth) acrylates of polyethylene glycol monoethers, N-vinyl-2-pyrrolidone, N-vinyl formamide, N-vinyl acetamide, 2-hydroxyethyl (meth)acrylate, hydroxypropyl acrylate, vinyl pyridine, N,N-diethylaminoethyl methacrylate, N,N-dimethylaminoethyl (meth)acrylate, N-t-butylaminoethyl acrylate, acrylic acid, methacrylic acid, itaconic acid, maleic acid, fumaric acid, vinyl benzoic acid, 2-carboxyethyl acrylate, 2-sulfoethyl (meth)acrylate, and 4-vinyl phenyl phosphonic acid. In yet another embodiment, the (c) monomers may be chosen from (meth)acrylic acid and N-vinyl-2-pyrrolidone.

The copolymer may optionally include units derived from other monomers to improve performance, reduce cost, or for other purposes, provided that such monomers are used in an amount that does not compromise the composition's reshapable effect. Examples of such other monomers may include vinyl esters, vinyl chlorides, vinylidene chlorides, styrenes, macromolecular monomers such as monoacrylic functional polystyrene and polydimethylsiloxane, and the like.

The composition may further comprise an appropriate cosmetically acceptable vehicle. The choice of vehicle is adapted to the method of application selected. The cosmetic vehicle appropriate for hair may be chosen from water, water miscible solvents such as lower alcohols, e.g., $C_1$ to $C_4$ branched and straight chain aliphatic alcohols, and combinations thereof. In one embodiment, the vehicle is a lower alcohol chosen from ethanol, n-propanol, and 2-propanol (IPA). When water miscible solvents and water are present, the solvent to water ratio may range from about 20:80 to about 90:10 weight/weight, such as from about 30:70 to about 85:15.

The vehicle may also comprise additional solvents. For example, other rapid evaporating solvents may be used, such as hexamethyldisiloxane (HMDS); cyclic silicones ($D_4$ and $D_5$); $C_4$–$C_{10}$ alkanes including isoparafins such as Permethyl 97A and Isopar C; acetone; hydrofluoroethers (HFEs) and the like.

The composition may also comprise additives such as gelling agents, foaming agents, and silicones. It is understood that the person skilled in the art will know how to choose the additional constituents and their amount in the composition according to the invention, such as the constituents of the composition, so as not to adversely affect or substantially affect its reshapable hair styling properties.

The inventive copolymers of the present invention may be prepared using emulsion polymerization, solution polymerization followed by an inversion step, and suspension polymerization. These methods use initiators that, through various techniques, are decomposed to form free radicals. Once in their radical form, the initiators react with the monomers, starting the polymerization process. The initiators are often called "free radical initiators." Various decomposition methods for the initiators are discussed first, followed by a description of the emulsion, solution, and suspension polymerization methods.

The initiator can be decomposed homolytically to form free radicals. Homolytic decomposition of the initiator can be induced by using heat energy (thermolysis), using light energy (photolysis), and/or using appropriate catalysts. Light energy can be supplied by means of visible or ultraviolet sources, including low intensity fluorescent black light lamps, medium pressure mercury arc lamps, and germicidal mercury lamps.

Catalyst induced homolytic decomposition of the initiator typically involves an electron transfer mechanism, resulting in a reduction-oxidation (redox) reaction. This redox method of initiation is described in Elias, Chapter 20 (detailed below). Initiators such as persulfates, peroxides, and hydroperoxides are more susceptible to this type of decomposition. Useful catalysts include, but are not limited to (1) amines, (2) metal ions used in combination with peroxide or hydroperoxide initiators, and (3) bisulfite or mercapto-based compounds used in combination with persulfate initiators.

Presently, in certain embodiments of the invention, the method of initiation comprises thermolysis or catalysis. Thermolysis can provide ease of control of the reaction rate and exotherm.

Useful initiators are described in Chapters 20 & 21 Macromolecules, Vol. 2, 2nd Ed., H. G. Elias, Plenum Press, 1984, New York, the disclosure of which is specifically herein by reference. Useful thermal initiators include, but are not limited to, the following: (1) azo compounds such as 2,2-azo-bis-(isobutyronitrile), dimethyl 2,2'-azo-bis-isobutyrate, azo-bis-(diphenyl methane), and 4-4'-azo-bis-(4-cyanopentanoic acid); (2) peroxides such as benzoyl peroxide, cumyl peroxide, tert-butyl peroxide, cyclohexanone peroxide, glutaric acid peroxide, lauroyl peroxide, and methyl ethyl ketone peroxide; (3) hydrogen peroxide and hydroperoxides such as tert-butyl hydroperoxide and cumene hydroperoxide; (4) peracids such as peracetic acid and perbenzoic acid; potassium persulfate; ammonium persulfate; and (5) peresters such as diisopropyl percarbonate.

Useful photochemical initiators include but are not limited to benzoin ethers such as diethoxyacetophenone, oximino-ketones, acylphosphine oxides, diaryl ketones such as benzophenone and 2-isopropyl thioxanthone, benzil and quinone derivatives, and 3-ketocoumarins as described by S. P. Pappas, J. Rad. Cur., July 1987, p.6, the disclosure of which is specifically incorporated herein by reference.

In one embodiment, the copolymers of the present invention can be made by emulsion polymerization, generally comprising a process where the monomers are dispersed in a continuous phase (typically water) with the aid of an emulsifier and polymerized with free-radical initiators, described above. Other components that are often used in this process include stabilizers (e.g., copolymerizable surfactants), chain transfer agents for minimizing and/or controlling the polymer molecular weight, and catalysts. The product of this type of polymerization is typically a colloidal dispersion of the polymer particles, often referred to as a "latex." In one embodiment of an emulsion polymerization process, a redox chemistry catalyst, such as sodium metabisulfite, used in combination with potassium persulfate initiator and ferrous sulfate heptahydrate, is used to start the polymerization at or near room temperature. Typically, the copolymer particle size is less than one micrometer, such as less than 0.5 micrometer.

In another embodiment, the copolymers of the present invention can be made by solution polymerization followed by an inversion step. In one illustrative solution polymerization method, the monomers and suitable inert solvents are charged into a reaction vessel. The monomers and the resultant copolymers are soluble in the solvent. After the monomers are charged, an initiator, such as a thermal free radical initiator, is added. The vessel is purged with nitrogen to create an inert atmosphere. The reaction is allowed to proceed, typically using elevated temperatures, to achieve a desired conversion of the monomers to the copolymer. In solution polymerization, the initiator used may comprise a thermally decomposed azo or peroxide compound for reasons of solubility and control of the reaction rate.

Suitable solvents for solution polymerizations include but are not limited to (1) esters such as ethyl acetate and butyl acetate; (2) ketones such as methyl ethyl ketone and acetone; (3) alcohols such as methanol and ethanol; (4) aliphatic and aromatic hydrocarbons; and (5) mixtures thereof. The solvent may be any substance which is liquid in a temperature range of about −10° C. to about 50° C., does not interfere with the energy source or catalyst used to dissociate the initiator to form free radicals, is inert to the reactants and product, and will not otherwise adversely affect the reaction. The amount of solvent, when used, is generally about 30 to about 80 percent by weight based on the total weight of the reactants and solvent. Preferably, the amount of solvent ranges from about 40 weight percent to about 65 weight percent, based upon the total weight of the reactants and solvent, to yield fast reaction times.

Copolymers prepared by solution polymerization can be inverted to yield dispersions of small average particle size, typically less than about one micrometer, such as less than about 0.5 micrometer. Inversion can occur in an aqueous carrier or aqueous solvent provided that (1) they contain ionic functionality or (2) they contain acidic or basic functionality, which on neutralization yields ionic functionality.

Copolymers containing acidic functionality are obtained by copolymerizing acidic monomers. Suitable acidic monomers include those containing carboxylic acid functionality such as acrylic acid, methacrylic acid, itaconic acid, etc.; those containing sulfonic acid functionality such as 2-sulfoethyl methacrylate; and those containing phosphonic acid functionality. Preferred acidic monomers include acrylic acid and methacrylic acid.

Copolymers containing basic functionality are obtained by copolymerizing basic monomers. Suitable basic monomers include those containing amine functionality such as vinyl pyridine; N,N-diethylaminoethyl (meth)acrylate; N,N-dimethylaminoethyl (meth)acrylate; and N-t-butylaminoethyl acrylate. Preferred basic monomers include N,N-dimethylaminoethyl (meth)acrylate.

Preferably the copolymer is prepared in a water-miscible solvent, which has a boiling point below 100° C., such as acetone or methyl ethyl ketone. Alternatively, a non-water-miscible polymerization solvent such as ethyl acetate may be used. The non-water-miscible polymerization solvent may be removed from the copolymer by using a rotary evaporator. The resulting copolymer can then be dissolved in a water-miscible solvent such as those described above or mixtures including isopropanol, methanol, ethanol, and tetrahydrofuran.

The resulting solutions are added with stirring to an aqueous solution of a base (in the case of copolymers containing the acidic functionality) or an acid (in the case of copolymers containing the basic functionality). Alternatively, the base or acid can be added to the polymer solution prior to adding water or being added to water. Suitable bases include (1) ammonia and organic amines, such as aminomethyl propanol, triethyl amine, triethanol amine, methyl amine, and morpholine, and (2) metal hydroxides, oxides, and carbonates, etc. Suitable acids include (1) carboxylic acids such as acetic acid, and (2) mineral acids, such as HCl. In the case of a volatile weak base (e.g., ammonia) or acid (e.g., acetic acid), the ionic group formed (an ammonium carboxylate) is non-permanent in nature. For example, for an acrylic acid containing polymer neutralized with aqueous ammonia, the polymer remains as the ammonium acrylate derivative when dispersed in water, but is thought to revert to its original free acid state as the coating dries on the surface. This is because there is equilibrium between the neutralized and free acid, which is shifted towards the free acid as the ammonia is driven off on drying.

In yet another embodiment, the copolymers of the present invention can be made by a suspension polymerization method. The suspension polymerization method for making the inventive copolymers can proceed in the absence of surfactants. Instead, colloidal silica in combination with a promoter may be used as the stabilizer. Using this process, surfactant-free copolymers can be obtained with a relatively narrow particle size distribution (preferably, no greater than about 20%).

In one embodiment, the method for suspension polymerization involves making a monomer premix comprising the (a), (b), and optional (c) and (d) monomers. The premix is combined with a water phase, such as deionized water, containing colloidal silica and a promoter. Amphiphilic polymers represent one class of useful promoters.

The pH of the mixture is adjusted so as to be in the range of 3 to 11, such as in the range of 4 to 6, without coagulation of the particles. For certain monomers, the initial pH of the mixture can be as low as about 2.5. This pH is low enough for the colloidal silica to stabilize the monomer droplet, but the final product may contain a small amount of coagulum. Similar observations can be made at high pH. It has been observed that when the mixture is treated with ammonia or hydrochloric acid to a pH ranging from about 4 to about 6, the reaction is more stable and the final product is basically free of coagulum.

The mixture is exposed to high shear, such as that capable in a Waring™ blender, to break the monomer droplets down to a diameter size of 1 micrometer or less. The shearing action is then reduced to a lower agitation (or temporarily stopped) to allow for the partial coalescence of the small droplets and formation of a suspension. Initiator is added. The silica-promoter mixture stabilizes the droplets and limits their coalescence yielding very uniform, and sometimes nearly monodisperse particles. The suspension polymerization is completed under moderate agitation and a stable, aqueous dispersion of acrylic particles is obtained.

The above described suspension polymerization has several advantages. For example, the method yields a copolymer with a narrow distribution of mean particle size and limited coalescence. When coalescence is present, the particles tend to migrate towards one another and can form large masses. Coalescence hampers the handling and transportation of the particles and thus is undesirable.

Also, the method allows for copolymers that withstand freezing temperatures, allowing them to be redispersed after thawing. It has been discovered that the copolymer is stable, i.e., does not coalesce when the same volume of alcohol (methanol or isopropanol) and water is used in the dispersion.

In another embodiment of the invention, the acrylic polymer has a glass transition temperature (Tg) ranging from about −100° C. to about 15° C. According to the present invention, the Tg of the acrylic polymer is obtained following the application of the acrylic copolymer in a simplex vehicle to a substrate and then drying. The glass transition temperature is determined by the Differential Scanning Calorimetric method (DSC).

In one embodiment of the invention, the acrylic copolymer may be present in an amount ranging from about 0.1 to about 40, such as from about 0.5 to about 15, weight percent of the total weight of the composition in order to provide a reshapable effect.

The composition according to the invention may comprise at least one other constituent, which is conventional in cosmetics, chosen from preservatives; perfumes; UV filters; active haircare agents; plasticizers; anionic, cationic, amphoteric, nonionic, and zwitterionic surfactants; hair conditioning agents such as silicone fluids, fatty esters, fatty alcohol, long chain hydrocarbons, emollients, lubricants, and penetrants such as lanolin compounds, protein hydrolysates, and other protein derivatives; anionic, cationic, amphoteric, nonionic, and zwitterionic polymers; dyes; tints; bleaches; reducing agents; pH adjusting agents; sunscreens; and thickening agents.

The compositions according to the invention can be provided in any form known from the prior art, which is appropriate for their application to the hair, including in the form of a vaporizable composition such as sprays and aerosols, mousse, gel, or lotion.

The composition may be in any of the conventional forms of cosmetic composition including, but not limited to, shampoos, hair rinses, permanent waving compositions, waving compositions, hair dye compositions, hair straightening compositions, hair fixing products, hair styling gel products, products to use before or after a hair dye treatment, products to use before or after a permanent waving treatment, hair straightening compositions, products to use before or after a hair straightening treatment, and fixing foams.

The composition according to the invention may be vaporizable, for example by a pump, or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term lower alcohol means a $C_1$ to $C_4$ aliphatic alcohol, preferably ethanol.

When the vaporizable composition according to the invention is an aerosol composition, it additionally comprises an appropriate amount of propellant. The propellant comprises compressed or liquefied gases, which are normally employed for the preparation of aerosol compositions. Suitable gasses include compressed air, carbon dioxide, nitrogen, and gases, which are soluble or otherwise in the composition, such as dimethyl ether, fluorinated or non-fluorinated hydrocarbons, and mixtures thereof.

The present invention additionally provides an aerosol device comprising a vessel comprising an aerosol composition, which comprises on the one hand a liquid phase (or juice) comprising at least one hair styling material as described above in an appropriate medium and on the other hand a propellant, and a dispenser for dispensing said aerosol composition.

The present invention additionally provides a method of treating keratinous fibers, especially hair, in which the composition according to the invention as defined above is applied to the hair before, during, or after the shaping of the hairstyle.

The compositions according to the invention can be rinsed off or not rinsed off the hair.

The present invention additionally provides the use of a composition as defined above in, or for the preparation of, a cosmetic reshapable hair styling formulation.

The determination of whether a composition with an acrylic copolymer according to the invention can provide a reshapable effect can be determined by an in vivo test.

Where the composition is in the form of a lotion, for example, the in vivo test proceeds as follows. The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cosmetic properties, and the reshapable effect. For example, once dried, the hair is brushed in different directions to remove the original styling. The hair is then brushed to restore the original styling. The process of removing the styling, restoring the styling, and evaluating the success of restoring the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10–20 different individuals.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The invention may be understood more clearly with the aid of the non-limiting examples that follow, and which constitute an advantageous embodiment of the compositions in accordance with the invention.

EXAMPLES

Hair compositions according to the invention were produced with different acrylic copolymers. Percentages given are by weight, unless otherwise specified.

1) Preparation of the Acrylic Copolymers

Examples 1 to 13 (Copolymers Made by Emulsion Polymerization)

Into a one liter Mortonized split resin flask was charged 100 grams of monomers (detailed in Table I below), 80 milligrams of carbon tetrabromide, 124.7 grams of deionized water, 200 milligrams of potassium persulfate, 64 milligrams of sodium metabisulfite, 1 gram of sodium dodecyl benzene sulfonate, and 2.5 g of Mazon SAM 211 alkylene polyalkoxy ammonium sulfate copolymerizable surfactant (available from PPG Industries, Pittsburgh, Pa.). The head was placed on the flask and a thermocouple, nitrogen inlet, and mechanical stirrer attached. The headspace was swept with nitrogen at 1 liter per minute while heating the contents with infrared lamps to about 30° C. and stirring at 250 rpm. About 1 gram of a solution of 28 milligrams ferrous sulfate heptahydrate in 50 grams deionized water was charged, the flask sealed, and a vacuum pulled on the flask three times, breaking it each time with nitrogen. After 15 or 20 minutes an exotherm is noted which peaks 20 to 25 minutes later at 55° C. to 65° C. Reactor temperature is increased to about 75° C. and held for one hour, then the resulting latex was filtered through doubled over cheesecloth into a jar. In all cases moderate levels of coagulum were noted around the thermocouple and stirring paddle.

TABLE I

Monomer Charges Used for Emulsion Polymerization

| Example | g 2-EHA | g IBOA | g AA | g MAA |
|---|---|---|---|---|
| 1 | 60 | 35 | 0 | 5 |
| 2 | 55 | 40 | 0 | 5 |
| 3 | 50 | 45 | 5 | 0 |
| 4 | 50 | 45 | 0 | 5 |
| 5 | 50 | 40 | 0 | 10 |
| 6 | 45 | 50 | 5 | 0 |
| 7 | 45 | 50 | 0 | 5 |
| 8 | 35 | 60 | 0 | 5 |
| 9 | 70 | 25 | 0 | 5 |
| 10 | 60 | 35 | 5 | 0 |
| 11 | 55 | 40 | 5 | 0 |
| 12 | 25 | 70 | 0 | 5 |
| 13 | 80 | 15 | 5 | 0 |

2-EHA = 2-ethylhexyl acrylate
IBOA = isobornyl acrylate
AA = acrylic acid
MAA = methacrylic acid Examples 14 to 17 (Copolymers Made by Solution Polymerization and Inversion in Water)

Into a 120 milliliter glass bottle was charged 24 grams of monomers (detailed in Table II below), 120 milligrams of carbon tetrabromide, 36 grams of methylethyl ketone, and 72 milligrams of azobis(isobutyronitrile). The contents of the bottle were swept with nitrogen at about 1 liter per minute for two minutes, then the bottle was capped and tumbled in a water bath for 24 hours at about 55° C. yielding a moderate viscosity solution. 15 grams (containing 6 grams of polymer or 8.3 milliequivalents of carboxylic acid) of the resulting solution was charged into a 250 milliliter round bottom flask containing a solution of 0.67 grams (7.5 milliequivalents, 90% neutralization) of 2-amino-2-methyl-1-propanol in 14 grams of deionized water with moderate agitation. The solvent was removed from the resulting dispersion by a rotary evaporator set at about 63° C. at a reduced pressure of 40 kilopascals yielding a milky white dispersion. The resulting dispersions were coated as described above.

TABLE II

Monomer Charges Used for Solution Polymerization with Inversion

| Example | g 2-EHA | g IBOA | g CHXMA | g AA |
|---|---|---|---|---|
| 14 | 12.6 | 9.0 | 0 | 2.4 |
| 15 | 11.4 | 10.2 | 0 | 2.4 |
| 16 | 10.8 | 0 | 10.8 | 2.4 |
| 17 | 8.4 | 0 | 13.2 | 2.4 |

CHXMA = cyclohexyl methacrylate

Examples 18 to 20 (Copolymers Made by Suspension Polymerization)

In one liter Mortonized split resin flask was charged 240 gram of a monomer mixture (detailed in Table II). Added to the flask was 6.9 g Ludox™ 50 (50% by wt colloidal silica in water, available from Aldrich, Milwaukee, Wis.), 360 g deionised water, 0.42 g adipic acid/diethanol amine condensate (a 50% solids used as a promoter, prepared according to the procedure disclosed in U.S. Pat. No. 5,238,736), and 0.08 g potassium dichromate. The head was placed on the flask and a thermocouple, nitrogen inlet, and mechanical stirrer attached. The entire content inside the flask is mixed. The pH is measured and adjusted by adding ammoninum hydroxide to a pH between 4 and 5. The mixture was then transferred to a Warring™ blender and exposed to high shear (about 22,000 rpm) for six minutes total, using shear for about two minutes at a time to avoid overheating the mixture.

The mixture was then returned to the Mortonized flask and 0.36 g of Vazo™ 64 (azo-bis(isobutyronitrile) initiator, available from E.I. du Pont de Nemours & Co., Wilmington, Del.) was added. A nitrogen purge was started and the mixture is agitated gently for several minutes to let the initiator dissolve. The agitation speed is adjusted to about 300 rpm and the temperature was set at about 60° C. The reaction started within minutes and was allowed to exotherm. After exotherming, the temperature was maintained at about 60° C. for about four hours.

TABLE III

Monomer Charges Used for Suspension Polymerization

| Example | Parts | g 2-EHA | g IBOA | g MAA |
|---|---|---|---|---|
| 18 | 50/45/5 | 120 | 108 | 12 |
| 19 | 55/40/5 | 132 | 96 | 12 |
| 20 | 60/35/5 | 144 | 84 | 12 |

Example 21

A 50/50 mixture of the emulsion from Example 19 and a dispersion comprising AQ 1350 by the Eastman Chemical Co. as disclosed in WO 98/38969 can be made.

Example 22

A 25/75 mixture of the emulsion from Example 19 and the emulsion from Example 20 can be made.

2) Preparation of the Hair Styling Compositions

Eleven hair styling compositions in accordance with the invention were prepared using the components and amounts in weight percent listed hereafter. The testing was conducted on several models with one part of the head receiving a reference composition and the other side of the head receiving the tested composition. The compositions were applied to wet hair after shampooing. The hair was then dried, brushed, and evaluated.

Reference:

| AQ 1350 | 4% active material |
|---|---|
| Water | qsp 100% |

Formulation A:

| Example 19 | 4% active material |
|---|---|
| Water | qsp 100% |

Formulation A imparted good hairstyling with good cosmetic properties and a reshapable effect but the latter was not as good as the reference.

Formulation B:

| Example 13 | 4% active material |
|---|---|
| Water | qsp 100% |

Formulation B imparted good hairstyling and a reshapable effect equal to the reference with adequate cosmetic properties.

Formulation C:

| Example 9 | 4% active material |
|---|---|
| Water | qsp 100% |

Formulation C imparted very good hairstyling and a reshapable effect. The latter and cosmetic properties were not as good as the reference.

Formulation D:

| Example 1 | 4% active material |
|---|---|
| Water | qsp 100% |

Formulation D imparted good hairstyling and a reshapable effect equal or better than the reference with adequate cosmetic properties.

Formulation E:

| Example 2 | 4% active material |
|---|---|
| Water | qsp 100% |

Formulation E imparted good hairstyling but poor reshapable effect and cosmetic properties compared to the reference.

Formulation F:

| Example 11 | 4% active material |
|---|---|
| Water | qsp 100% |

Formulation F imparted adequate hairstyling and a good reshapable effect but the hairstyling and cosmetic properties were not as good as the reference.

Formulation G:

| Example 10 | 4% active material |
|---|---|
| Water | qsp 100% |

Formulation G imparted good hairstyling but poor reshapable effect and cosmetic properties compared to the reference.

Formulation H:

| | |
|---|---|
| Example 3 | 4% active material |
| Water | qsp 100% |

Formulation H imparted good hairstyling and a reshapable effect better than the reference with good cosmetic properties.

Formulation I:

| | |
|---|---|
| Example 1 | 2% active material |
| Example 3 | 2% active material |
| Water | qsp 100% |

Formulation I imparted very good hairstyling and a very good reshapable effect with correct cosmetic properties.

Formulation J:

| | |
|---|---|
| Example 1 | 2% active material |
| Example 10 | 2% active material |
| Water | qsp 100% |

Formulation J imparts very good hairstyling and very good reshapable effect with medium cosmetic properties.

Formulation K:

| | |
|---|---|
| Example 2 | 2% active material |
| Example 3 | 2% active material |
| Water | qsp 100% |

Formulation K imparts very good hair styling and very good reshapable effect with medium cosmetic properties.

What is claimed is:

1. A reshapable hair styling composition comprising at least one acrylic copolymer comprising:
   (a) from about 20 to about 80 weight percent of units derived from ethyl hexyl (meth)acrylate,
   (b) from about 5 to about 65 weight percent of units derived from isobornyl acrylate, and
   (c) from 1 to about 15 weight percent of units derived from (meth)acrylic acid, wherein the ratio of ethyl hexyl (meth)acrylate derived units to isobornyl acrylate derived units ranges from about 0.5:1 to about 6:1,
   wherein said composition provides a reshapable effect.

2. The composition according to claim 1, wherein said at least one acrylic copolymer is present in an amount ranging from about 0.1 to about 40 weight percent of the total weight percent of the composition.

3. The composition according to claim 2, wherein the amount of said at least one acrylic copolymer ranges from about 0.5 to about 15 weight percent.

4. The composition according to claim 1, wherein said at least one acrylic copolymer has a Tg ranging from about −100° C. to about 15° C.

5. The composition according to claim 1, wherein the composition further comprises at least one additional polymer.

6. The composition according to claim 5, wherein said at least one additional polymer is chosen from anionic, cationic, amphoteric, nonionic, and zwitterionic polymers.

7. The composition according to claim 1, further comprising at least one other constituent, which is conventional in cosmetics, chosen from preservatives, perfumes, UV filters, active haircare agents, plasticizers, anionic, cationic, amphoteric, noinionic, and zwitterionic surfactants, hair conditioning agents such as silicone fluids, fatty esters, fatty alcohol, long chain hydrocarbons, emollients, lubricants and penetrants such as lanolin compounds, protein hydrolysates, and other protein derivatives, dyes, tins, bleaches, reducing agents, pH adjusting agents, sunscreens, and thickening agents.

8. A composition according to claim 1, wherein said reshapable hair styling composition is in the form of a spray, aerosol, mousse, gel, or lotion.

9. An aerosol device comprising a vessel, which comprises:
   (1) an aerosol composition, which provides a reshapable effect and comprises a liquid phase comprising at least one composition according to claim 17 and a propellant, and
   (2) a dispenser.

10. A method of cosmetically treating hair, comprising applying to the hair before, during, or after shaping of a hairstyle of said hair a composition according to claim 1, wherein said composition provides a reshapable effect.

11. A method of reshaping hair, comprising:
   (1) applying to the hair before, during, or after the initial shaping of the hairstyle of a composition according to claim 1,
   wherein said composition provides a reshapable effect, and
   (2) thereafter shaping the hairstyle at least once, wherein no additional composition or heat is added.

* * * * *

UNITED STATES PATENT AND TRADEMARK OFFICE
CERTIFICATE OF CORRECTION

PATENT NO. : 6,689,346 B1  Page 1 of 1
DATED : February 10, 2004
INVENTOR(S) : Isabelle Rollat et al.

It is certified that error appears in the above-identified patent and that said Letters Patent is hereby corrected as shown below:

Column 14,
Line 36, "claim 17" should read -- claim 1 --.

Signed and Sealed this

Thirteenth Day of April, 2004

JON W. DUDAS
*Acting Director of the United States Patent and Trademark Office*